United States Patent [19]

Nardella

[11] Patent Number: 5,335,668
[45] Date of Patent: Aug. 9, 1994

[54] DIAGNOSTIC IMPEDANCE MEASURING SYSTEM FOR AN INSUFFLATION NEEDLE

[75] Inventor: Paul C. Nardella, North Easton, Mass.

[73] Assignee: Medical Scientific, Inc., Taunton, Mass.

[21] Appl. No.: 56,364

[22] Filed: Apr. 30, 1993

[51] Int. Cl.⁵ ................................................ A61B 5/05
[52] U.S. Cl. ........................................ 128/734; 128/747
[58] Field of Search ............ 128/639, 642, 734, 774, 128/780, 782, 747

[56] References Cited

U.S. PATENT DOCUMENTS

| | | | |
|---|---|---|---|
| 3,480,003 | 11/1969 | Crites | 128/734 X |
| 3,913,583 | 10/1975 | Bross | 128/303.14 |
| 4,114,623 | 9/1978 | Meinke et al. | 128/303.14 |
| 4,126,137 | 11/1978 | Archibald | 128/303.14 |
| 4,193,408 | 3/1980 | Fujino | 128/734 |
| 4,271,837 | 6/1981 | Schuler | 128/303.14 |
| 4,474,179 | 10/1984 | Koch | 128/303.17 |
| 4,498,481 | 2/1985 | Lemke | 128/734 |
| 4,535,773 | 8/1985 | Yoon | 604/51 |
| 4,630,615 | 12/1986 | Yomtov | 128/734 |
| 4,651,280 | 3/1987 | Chang et al. | 364/413 |
| 4,658,819 | 4/1987 | Harris et al. | 128/303.13 |
| 4,676,774 | 6/1987 | Semm et al. | 604/26 |
| 4,712,544 | 12/1987 | Ensslin | 128/303.14 |
| 4,729,385 | 3/1988 | Juncosa et al. | 128/734 |
| 4,805,621 | 2/1989 | Heinze et al. | 128/419 |
| 4,869,717 | 9/1989 | Adair | 604/51 |
| 4,874,362 | 10/1989 | Wiest et al. | 604/26 |
| 4,911,174 | 3/1990 | Pederson et al. | 128/695 |
| 4,934,377 | 6/1990 | Bova et al. | 128/696 |
| 4,966,578 | 10/1990 | Baier et al. | 604/26 |
| 5,109,870 | 5/1992 | Silny et al. | 128/734 X |
| 5,190,517 | 3/1993 | Zieve et al. | 604/22 |

FOREIGN PATENT DOCUMENTS

0508453A1 10/1992 European Pat. Off. .

*Primary Examiner*—Angela D. Sykes
*Attorney, Agent, or Firm*—Lahive & Cockfield

[57] ABSTRACT

A diagnostic impedance measuring system having an elongate tissue-penetrating probe member with a plurality of axially spaced reference electrodes disposed about a distal portion of the probe. The reference electrodes measure the impedance of the biological tissue adjacent each electrode. A first comparator element compares the measured impedance of at least a first and a second of the reference electrodes, and the comparator generates a first signal indicative of the impedance difference between the two electrodes. A second comparator element compares the measured impedance between either the first or second electrode and one additional electrode, and generates a second signal indicative of the impedance difference between the two electrodes. A third comparator element compares the first and second signals and generates a third signal indicative of the impedance difference between the two signals. The third signal communicates with a signal evaluation element that determines the relative position of the probe within a patient's body.

19 Claims, 3 Drawing Sheets

DIAGNOSTIC IMPEDANCE MEASURING SYSTEM FOR AN INSUFFLATION NEEDLE

BACKGROUND OF THE INVENTION

This invention relates generally to the determination of the relative location of a probe within a human or animal body. More particularly, the present invention relates to a device and method for determining the relative location of a probe within the human or animal body by measuring or monitoring the biological impedance located adjacent to the distal end of the probe.

One type of probe generally used during endoscopic procedures is an insufflation needle. Insufflation needles are commonly known and are used during certain surgical procedures to insufflate the abdominal cavity with a vapor or gas. Typically, insufflation needles comprise an inner cannula and an outer cannula. The inner cannula extends beyond the distal tip of the outer cannula and typically has a blunt distal end. The outer cannula has a needle point with a cutting tip for easy penetration of the skin and tissue underlying the abdominal wall. The outer cannula expands into a hub section at the proximal end that houses a biasing mechanism. The inner cannula is disposed within the outer cannula and includes a hollow tube having a distal end that is normally blunt, to avoid puncturing intra-abdominal structures. The distal end of the inner cannula has a side port hole located above the distal tip of the outer cannula through which vapor or gas may flow. When the tip of the insufflation needle is subject to an axial load, as a result of contacting tissue on or within the abdominal wall, the blunt end of the inner cannula is forced within the outer cannula, exposing the sharp cutting end of the outer cannula. After the insufflation needle pierces the abdominal wall structures and enters the abdominal cavity, the inner cannula is propelled forward by the biasing mechanism. The insufflation gas is then able to be delivered through the port hole to the intra-body cavity.

The use of the insufflation needle in the typical manner has several potential drawbacks. The surgeon must estimate the location of the needle within the abdomen as the needle is being inserted. This approach can result in the accidental puncture of an intra-abdominal structure, such as the bowel, liver or major blood vessel, by the cutting tip of the outer cannula.

As the above described and other prior art systems have proven less than optimal, an object of this invention is to provide an impedance measuring system for use with a surgical probe to measure the relative impedance of intra-abdominal structures. Another object of the invention is to provide an impedance measuring system that is easily adaptable to surgical probes. Still another object of the invention is to provide a reliable means of determining whether an internal cavity has been reached. Yet another object of the invention is to provide an additional safeguard against the accidental puncture of intra-abdominal structures. Other general and more specific objects of this invention will in part be obvious from the drawings and descriptions which follow.

SUMMARY OF THE INVENTION

These and other objects are attained by the invention which provides, in one embodiment, an impedance measuring system having an elongate tissue-penetrating probe member with a plurality of axially spaced reference electrodes disposed about a distal portion of the probe. The reference electrodes measure the impedance of the biological tissue adjacent to each electrode. A first comparator element compares the measured impedance of at least a first and a second of the reference electrodes, and the comparator generates a first signal indicative of the impedance difference between the two electrodes. A second comparator element compares the measured impedance between either the first or second electrode and one additional electrode, and generates a second signal indicative of the impedance difference between the two electrodes. A third comparator element compares the first and second signals and generates a third signal indicative of the impedance difference between the two signals.

The third signal can be either a NULL signal, which indicates that the impedance difference between the first and second signals is zero, or a non-NULL signal, which indicates that the difference between the first and second signals is greater or less than zero.

The impedance measuring system can be used in conjunction with a generator that supplies the reference electrodes with a diagnostic level of energy, insufficient to cut or cauterize biological tissue. A signal evaluation element is also used in conjunction with the foregoing elements to determine the relative position of the probe within a patient's body. According to one embodiment, the evaluation element can comprise an audible signal that sounds whenever the third signal is a NULL signal. Other embodiments include a single comparator element that compares the impedance of the biological tissue measured at the electrodes and generates an output signal indicative of the impedance difference.

In one particularly preferred embodiment, the probe member may be an insufflation needle.

Further embodiments of the invention will be evident from the above summary and from the description which follows.

BRIEF DESCRIPTION OF THE DRAWINGS

The foregoing and other aspects of the invention may be more fully understood from the following description, when read together with the accompanying drawings in which.

DETAILED DESCRIPTION OF THE INVENTION

Figure 1:
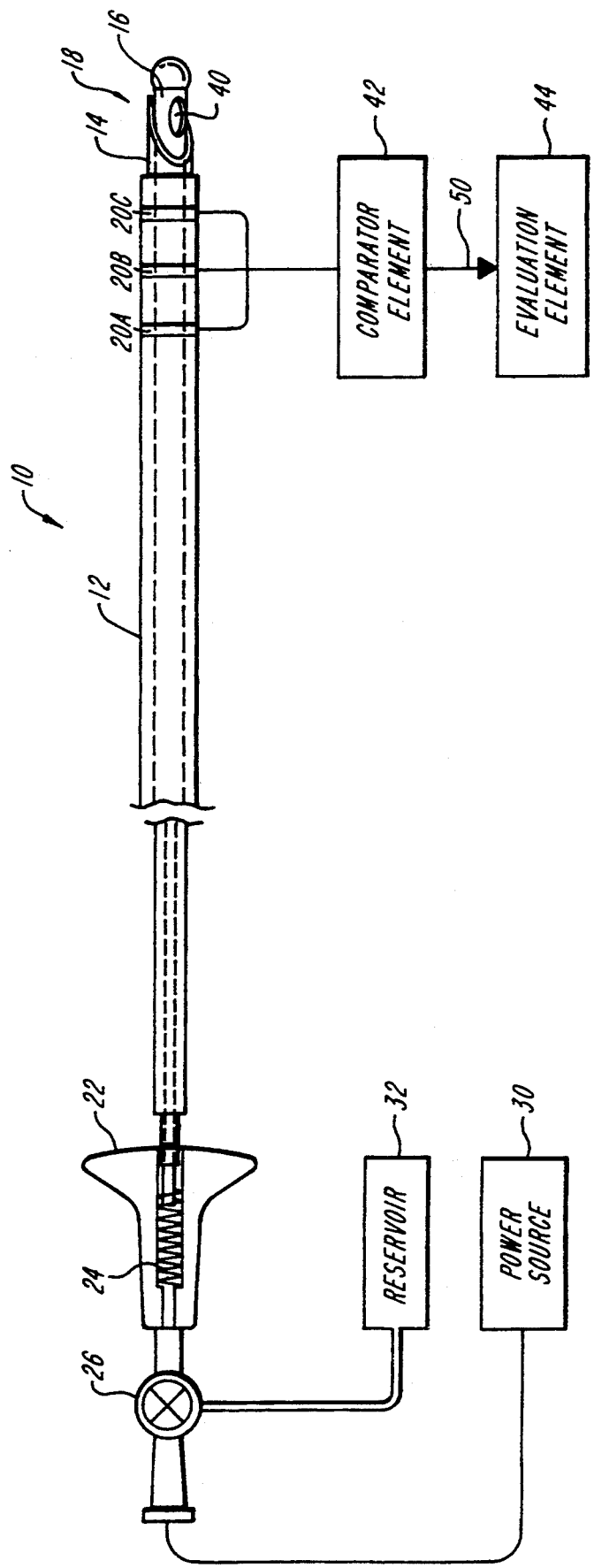
FIG. 1 illustrates the diagnostic impedance measuring system of the present invention.

FIG. 1 illustrates the electrosurgical probe and impedance measuring system 10 for which a preferred embodiment of the present invention is suitable for use. The system 10 comprises a power source 30, a reservoir 32, an elongate probe 12, a comparator element 42 and an evaluation element 44. In one embodiment, the probe 12 is an insufflation needle comprising an outer cannula 14 having a cutting tip 18, an inner cannula 16 having a side port hole 40, a biasing mechanism 24, reference electrodes 20A-C, and a valve 26. The power source 30 is in electrical communication with the reference electrodes 20A-C and the evaluation element 44. The device is adapted to deliver an insufflation vapor or gas from reservoir 32 through the probe 12 to an intrabody cavity such as the abdomen.

The reference electrodes 20A-C are in electrical communication with the comparator element 42, and the comparator element 42 communicates with the evaluation element 44 via signal 50. FIG. 1 illustrates comparator element 42 and evaluation element 44 adjacent the distal end of the probe 12 for ease of illustration. Preferably, comparator element 42 and evaluation element 44 are associated with power source 30.

The probe member 12 is an elongate member having a hub portion or handle 22 at its proximal end. An outer cannula 14 preferably is integral or associated with the handle and extends from the handle. The distal end of the outer cannula 14 has a chamfered end forming a cutting tip 18. An inner cannula is disposed within the outer cannula 14. The inner cannula is also an elongate member having a proximal end adjacent to the handle 22 and a distal end that is able to protrude from the distal end of the outer cannula 14. Preferably, the inner cannula 16 is biased to a position whereby it extends from the distal end of the outer cannula 14. The biasing force can be provided by a mechanism, e.g., a helically coiled spring 24, that is coupled to the proximal end of the inner cannula 16. Although the inner cannula 16 is biased to extend from the outer cannula 14, the inner cannula 16 can be retracted upon the placement of a sufficient axial load on the distal end of the inner cannula.

The inner cannula 16 preferably has a blunt distal end that is biased to extend beyond the outer cannula 14. The distal end of inner cannula 16 has a side port 40 for discharging an insufflation gas, preferably $CO_2$ gas, into an intra-body cavity. When the inner cannula 16 is subjected to an axial load, such as by contact with tissue, it is retracted within outer cannula 14 and the side port 40 is occluded and is unable to deliver the insufflation gas to the intra-body cavity. However, when the axial load is removed, the inner cannula is again biased to an extended position and a gas is able to be delivered through port 40.

The delivery of an insulation gas from reservoir 32 through the probe 12 can be achieved by methods well known in the art. Normally a valve 26 can be used to control the flow rate of the insufflation gas.

The probe 12 preferably has disposed about its distal end three reference electrodes 20A-C. The electrodes 20A-C can be placed about the outer cannula 14 in any conventional manner, but an annular orientation of each of the three electrodes is preferred. Those of ordinary skill in the art will realize that the electrodes need not be annular, but can also comprise helical or point electrodes. The electrodes 20A-C can be placed anywhere along the probe 12, but are preferably disposed in close proximity to the cutting tip 18 as illustrated in FIG. 1.

Further, the electrodes 20A-C are preferably electrically isolated from each other and from the probe 12. The reference electrodes are spaced about 2 to 6 mm apart, but it should be understood that the spacing may vary depending upon the depth and type of the biological tissue through which the probe must penetrate, and the sensitivity required of the electrodes. The present system 10 can also be used to determine the type and relative location of different layers of tissue.

The electrodes are preferably made from a medically compatible, highly conductive material such as gold, silver, or platinum. However, it is also possible to use less conductive electrode material such as stainless steel, or other highly resistive materials such as titanium. Alternatively, the electrodes can be made of an electrically conductive plating (e.g., gold, silver, or platinum) disposed upon an insulating material such as a polymer.

A power source 30, such as an electrosurgical generator, supplies a diagnostic level of electrosurgical energy, e.g., radio frequency energy, to the reference electrodes 20A-C. The electrosurgical generator can be any one of a variety of commercially available units.

As noted, the electrosurgical generator 30 is in electrical communication with the electrodes 20A-C via electrical leads (not shown). The electrical leads can be placed within the outer cannula 14. Alternatively, the leads can extend along the outside of the outer cannula 14, while being disposed within a non-conductive sheath. The sheath can be made of any suitable non-conductive material such as rubber or plastic.

The reference electrodes 20A-C also are in electrical communication with the comparator element 42 which preferably is associated with power source 30. The comparator element 42, compares the impedance measured by the electrodes 20A-C and generates an output signal 50 indicative of the difference in impedance adjacent the electrodes 20A-C. The evaluation element 44 receives the output signal 50 and determines whether the relative position of the probe 12 is disposed in a medium with varying impedance, or whether it is disposed in a medium of uniform impedance. The evaluation element is described in further detail below.

The voltage delivered across the electrodes 20A-C is preferably between 0.5 V and 3.0 V, and most preferably is about 2.0 V. The current delivered through the reference electrodes is preferably between 1.0 mA and 10 mA, and most preferably about 3.0 mA. Preferably, the amount of electrosurgical energy delivered through electrodes 20A-C is of a non-therapeutic magnitude and is not effective to cut or cauterize tissue. However, it is possible to construct a system that is able to cut, coagulate, and measure tissue, while also monitoring the differential impedance.

Figure 2:
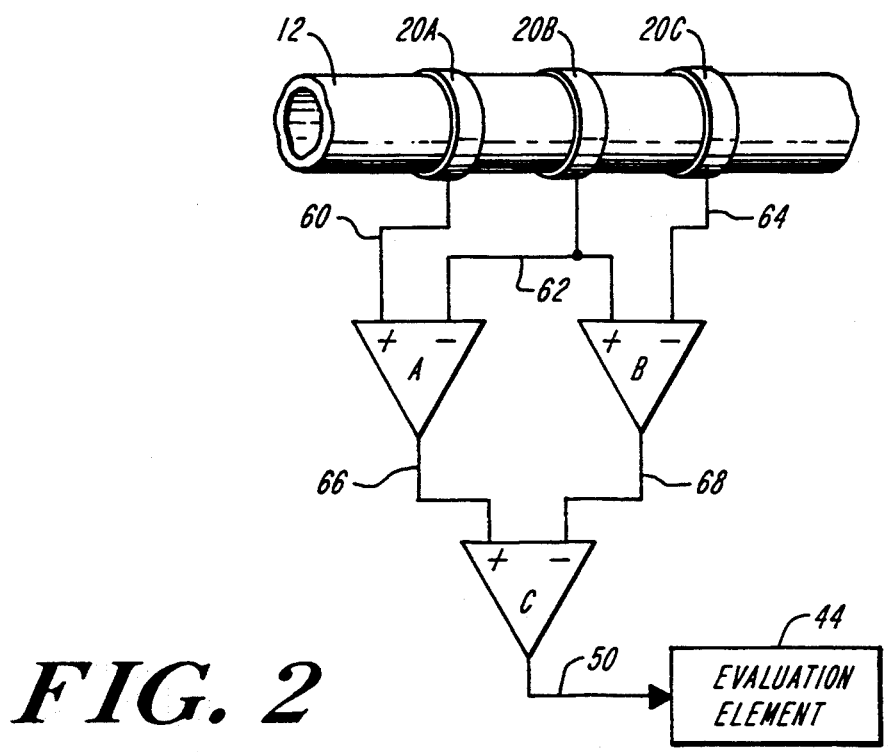
FIG. 2 shows a schematic circuit diagram of the impedance measuring circuit of the present invention.

FIG. 2 depicts a schematic circuit diagram of the comparator element 42 according to a preferred embodiment of the invention. The reference electrodes 20A-C of probe 12 are in electrical communication with comparator A and comparator B via electrical leads 60,62,64. Comparator A generates a first signal 66 that is coupled to the positive (+) input terminal of comparator C, and comparator B generates a second signal 68 that is coupled to the negative (−) or inverting input terminal of comparator C. The comparator C generates a third signal 50 indicative of the difference between the first signal 66 and the second signal 68. The third signal 50 is conveyed to the evaluation element 44.

The probe 12 of the present invention can be any type of tissue-penetrating probe. In one preferred embodiment, however, probe 12 comprises an insufflation needle useful to penetrate tissue to access and insufflate a body cavity such as the abdomen. During use of probe 12 as an insufflation needle, the electrosurgical generator supplies a selected voltage to the reference electrodes 20A-C. As the probe 12 penetrates tissue, the voltage across each electrode will vary in relation to the impedance of the corresponding biological tissue. This voltage change will be conveyed by the electrical leads 60,62,64 to comparator A and comparator B. Those of ordinary skill in the art will understand that the voltages presented at the inputs of comparators A and B are representative of and a function of the impedance of the tissue adjacent the needle electrodes 20A–C.

In the embodiment illustrated in FIG. 2, the voltage representative of the tissue impedance adjacent the cutting tip 18 is conveyed from electrode 20A to the positive (+) input terminal of comparator A along electrical lead 60. The tissue impedance measured at electrode 20B is conveyed to the negative (−) input terminal of comparator A and the positive (+) input terminal of comparator B via lead 62. The tissue impedance measured at electrode C is conveyed to the negative (−) input terminal of comparator B via lead 64.

Comparator A generates a first signal 66 indicative of the difference in impedance between the electrodes coupled to the input terminals. In the illustrated embodiment, signal 66 is indicative of the difference in impedance between electrode 20A and electrode 20B. Similarly, the second signal 68 generated by comparator B is indicative of the difference in impedance between electrode 20B and electrode 20C. Signals 66 and 68 are coupled to the positive (+) and negative (−) input terminals of comparator C, respectively. Comparator C generates a third signal 50 in response to the two input signals 66,68. The third signal 50 is indicative of the difference in impedance between the first and second signals 66,68. According to a preferred embodiment, the third signal 50 can be either a NULL or a non-NULL signal. The comparator C will generate a NULL signal when the first and second signals 66,68 are representative of substantially the same impedance value. Likewise, when the two signals 66,68 are representative of different impedance values, the comparator C will generate a non-NULL signal.

As illustrated, the third signal 50 is communicated to the evaluation element 44. The evaluation element 44 can be any apparatus or device that indicates to the surgeon or system user the representative impedance value conveyed by signal 50. For example, the evaluation element 50 can provide an audible alarm that sounds when the signal 70 is either a NULL or a non-NULL signal. Another embodiment can include a visual light, e.g., an LED, that blinks in the presence or absence of a NULL signal. Additionally, the evaluation element 44 can be an oscilloscope or a digital monitor. Other embodiments will be readily recognizable to one of ordinary skill in the art.

As noted, a NULL signal indicates that the probe 12 is in a medium of substantially homogeneous impedance while a non-NULL signal indicates that the electrodes 20A–C on probe 12 are in media of differing impedance. When a non-NULL signal is present, this is an indication that the electrodes 20A–C on probe 12 are in different types of tissue, and that the probe has not fully penetrated the abdominal wall. When a NULL signal is present, it is probable that the probe has penetrated the abdominal wall and that electrodes 20A–C are in the same medium, i.e., within the abdominal cavity.

It is understood that the circuit depicted in FIG. 2 is merely illustrative and can be modified in any number of ways to function equivalently. One skilled in the art will also appreciate the various combination the reference electrodes 20A–C can be applied to the two comparators A, B. Additionally, as few as two electrodes can be employed by the present invention to measure the difference in impedance. In a preferred embodiment, three electrodes 20A–C are used.

Figure 3:
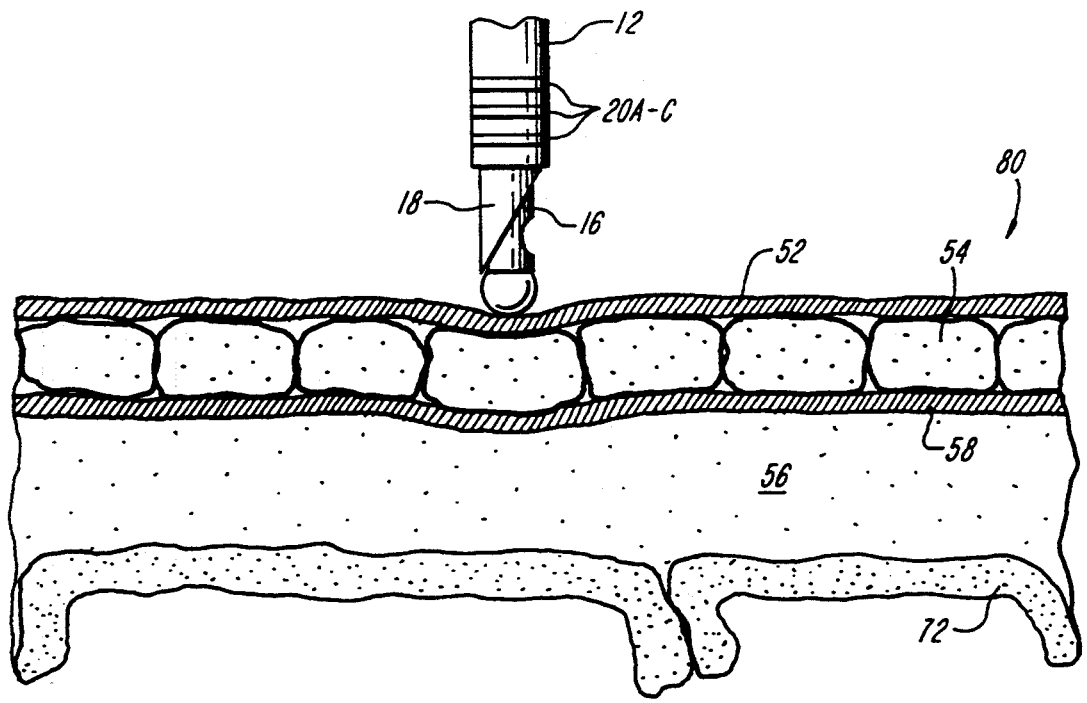
FIG. 3 is a diagrammatical view of a portion of the abdomen showing the insertion of the insufflation needle of FIG. 1.
Figure 4:
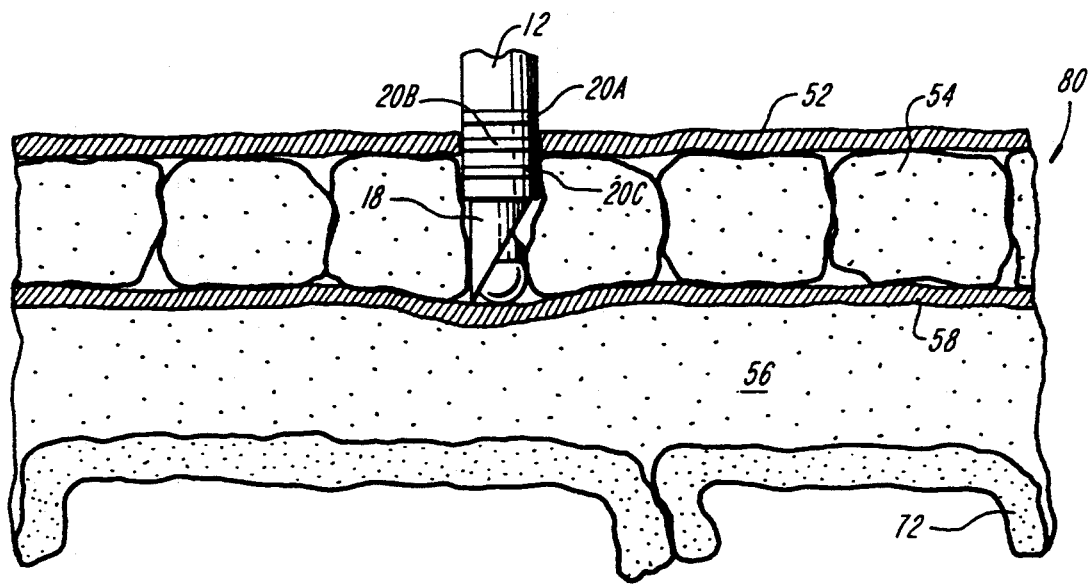
FIG. 4 is a diagrammatical view of a portion of the insufflation needle piercing the abdominal wall.
Figure 5:
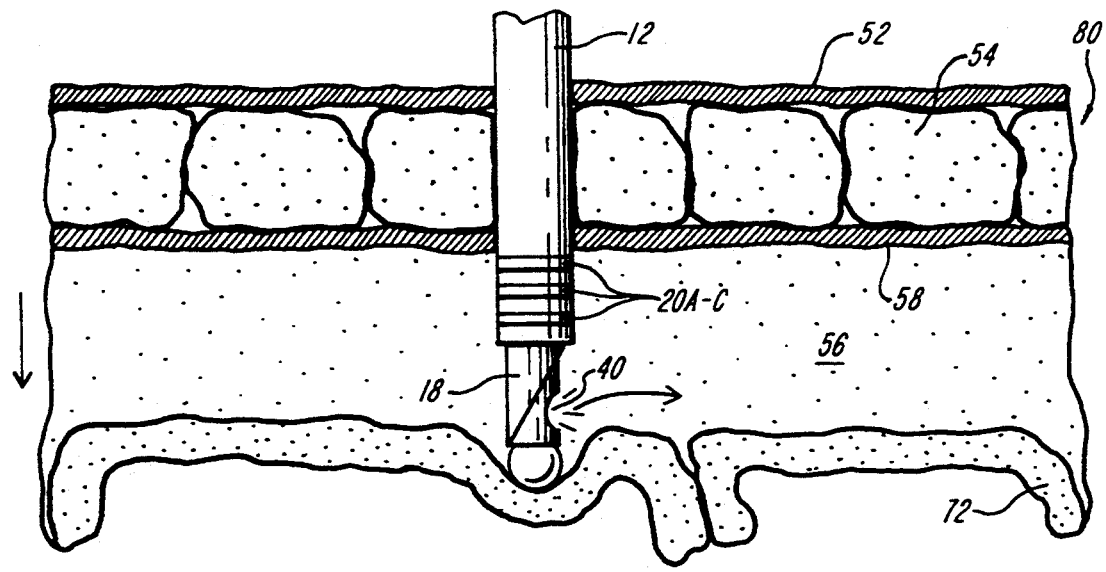
FIG. 5 is a diagrammatical view of the insufflation needle positioned within the abdominal cavity.

FIGS. 3–5 depict cross-sectional side views of the abdominal wall 80, and the penetration thereof by probe 12. The side views show several fundamental structures of the abdominal wall, and the tissue components depicted in FIGS. 3–5 are only meant to illustrate the operating environment of the present invention. Referring to FIG. 3, the abdominal wall 80 generally comprises skin 52, fat 54, and peritoneum 58. The abdominal cavity 56 and an internal abdominal structure 72 (e.g., the intestine) are also illustrated. To insert the insufflation 12 into the abdomen, the blunt end of the inner cannula 16 is pressed against the skin 52 of the abdominal wall 80. The needle 12 is then thrust downwardly, thereby disposing the inner cannula in the retracted position, while simultaneously exposing the cutting tip 18 of the outer cannula 14 to the skin 52. The cutting tip 18 of the needle 12 pierces the skin 52 and fat 54 as it travels downwardly towards the cavity 56 (see FIG. 4). The needle then passes through the peritoneum 58 and into the abdominal cavity 56. Once the needle passes through the peritoneum 58, the axial load that biases the inner cannula 16 in the retracted position is removed, and the biasing mechanism 24 propels the inner cannula downward into the abdominal cavity 56, as shown by the arrow in FIG. 5. The inner cannula 16 is then disposed in the extended position, exposing the side port hole 40. A gas is then insufflated into the cavity 56 through the port hole 40.

As the probe 12 passes through different types of biological tissue, the reference electrodes 20A–C measure the impedance of the tissue adjacent each respective electrode. Since different biological tissue types possess different inherent impedances, the three comparators A,B,C can detect different levels of impedance. For example, as the insufflation needle passes through the abdomen, the electrodes 20A–C are in contact with different biological tissue representative of different levels of impedance. Referring to FIG. 4, electrode 20C can contact fat 54, while electrode 20B contacts skin 52, and electrode 20A contacts a gas. The electrodes 20A–C thus convey different impedance values to the input terminals of comparators A and B of FIG. 2. As a result, the impedance signals 66 and 68 correspond to different impedance values, and the comparator C will generate a non-NULL signal.

Once the probe 12 is thrust entirely through the abdomen and into the abdominal cavity, the reference electrodes 20A–C will be exposed to a homogenous biological medium, as shown in FIG. 5. This homogeneity of medium results in a NULL signal being generated by comparator C, since the reference electrodes 20A–C are measuring the same impedance level. The generation of a NULL signal actuates the evaluation element 44. The evaluation element 44 then either sounds an audible alarm or trips a visible light. Either one of these events informs the surgeon that the abdominal cavity 56 has been reached. If the surgeon continues to drive the probe 12 into the patient, electrode 20C will eventually contact an internal organ, producing a nonhomogenous environment. This nonhomogeneity of medium results in a non-NULL signal being generated by comparator C, since the reference electrodes 20A–C are again measuring different impedance levels.

From the foregoing, the advantages of this invention are apparent and obvious. A disposable insufflation needle 12 can be used to pierce the abdominal wall and be positioned within the abdominal cavity, while simultaneously ensuring that internal structures are not damaged. The protection of internal organs is accomplished by the system of the present invention. Thus, during insertion of the needle 12, the reference electrodes 20A–C measure the impedance of the tissue adjacent the distal end of the outer cannula 14. The surgeon inserts the needle 12 until the comparator C generates a NULL signal indicative of a homogenous medium, e.g., placement within the abdominal cavity. The NULL signal actuates the evaluation element 44 which, in turn, trips an audible or visual alarm.

It will also be apparent to one of ordinary skill in the art that the invention can be used to monitor the progress of the probe 12 through different tissue types and different tissue types. That is changes in impedance will indicate passage through fat tissue, muscle tissue, connective tissue, and other tissue types.

In accordance with the above description, the invention attains the objects set forth. It is further intended that all matter and the description and drawings be interpreted as illustrative and not in a limiting sense. While various embodiments of the invention have been described in detail, other alteration obvious to those skilled in the art are intended to be embraced within the spirit and scope of the invention. For example, the number of electrodes used to measure the impedance of biological tissue may vary. Similarly, the number of comparators employed can be changed. The invention is to be defined, therefore, not by the preceding detailed description but by the claims that follow.

What is claimed as new and desired to be secured by Letters Patent is:

1. A diagnostic impedance measuring system comprising:
    an elongate tissue-penetrating insufflation needle having a distal end and a proximal end;
    a plurality of axially spaced reference electrodes disposed about the distal end of the insufflation needle;
    means for supplying a diagnostic level of energy to the electrodes;
    first comparator means for comparing the measured impedance adjacent at least a first and a second of the reference electrodes and generating a first signal indicative of the impedance difference therebetween;
    second comparator means for comparing the measured impedance adjacent either the first or second reference electrode and one additional reference electrode, and generating a second signal indicative of the impedance difference therebetween;
    third comparator means for comparing the first and second signals and generating a third signal indicative of the impedance difference between the first and second signals; and
    means for evaluating the third signal to determine the relative position of the insulation needle within a patient's body.

2. The system of claim 1 wherein the means for supplying diagnostic level of energy to the electrodes communicates with an electrosurgical generator.

3. The system of claim 1 wherein the third signal indicative of the impedance difference between the first and second signals is one of:
    a NULL signal indicating that the difference in impedance between the first and second signals is zero, and
    a non-NULL signal indicating that the impedance difference between the first and second signals is greater or less than zero.

4. The system of claim 3 wherein the means for evaluating the third signal generates an audible signal when the third signal is a non-NULL signal.

5. The system of claim 1 wherein the voltage delivered across the reference electrodes is in the range of 0.5 to 3.0 volts.

6. The system of claim 1 wherein the current delivered through the reference electrodes is in the range of 1.0 mA to 10 mA.

7. The system of claim 1 wherein three reference electrodes are positioned at the distal end of the insufflation needle and are axially spaced apart from each other by about 2 to 6 mm.

8. A diagnostic impedance measuring system for determining the relative position within a patient's body of an insufflation needle having a proximal end and a distal end, comprising:
    an electrosurgical generator:
    a plurality of axially spaced reference electrodes disposed upon a distal end of the insufflation needle;
    comparator means in electrical communication with the reference electrodes for comparing the impedance measured adjacent the electrodes and generating an output signal indicative of the impedance difference; and
    means for evaluating said output signal to determine the relative position of the insufflation needle within the patient's body.

9. The system of claim 8 wherein the electrosurgical generator delivers a diagnostic level of energy to the reference electrodes.

10. The system of claim 8 wherein the output signal indicative of the impedance difference is one of:
    a NULL signal indicating that the impedance difference is zero, and
    a non-NULL signal indicating that the impedance difference is greater or less than zero.

11. The system of claim 10 wherein the means for evaluating the output signal generates an audible signal when the output signal is a non-NULL signal.

12. The system of claim 8 wherein the voltage delivered across the reference electrodes is in the range of 0.5 to 3.0 volts.

13. The system of claim 8 wherein the current delivered through the reference electrodes is in the range of 1.0 mA to 10 mA.

14. A diagnostic impedance measuring device comprising:
    an elongate tissue-penetrating insulation member having a distal end and a proximal end;
    a plurality of axially spaced reference electrodes disposed about the distal end of the insufflation needle;
    means for supplying a diagnostic level of energy to the electrodes;
    first comparator means for comparing the measured impedance adjacent at least a first and a second of the reference electrodes and generating a first signal indicative of the impedance difference therebetween;
    second comparator means for comparing the measured impedance adjacent one of the first and second reference electrode and one additional reference electrode, and generating a second signal indicative of the impedance difference therebetween; and third comparator means for comparing the first and second signals and generating a third signal indicative of the impedance difference between the first and second signals.

15. The system of claim 14 wherein the means for supplying diagnostic energy to the electrodes communicates with an electrosurgical generator.

16. The system of claim 14 wherein the third signal indicative of the impedance difference between the first and second signals is one of:

a NULL signal indicating that the difference in impedance between the first and second signals is zero, and a non-NULL signal indicating that the difference in impedance between the first and second signals is greater or less than zero.

17. The system of claim 14 wherein the voltage delivered across the reference electrodes is in the range of 0.5 to 3.0 volts.

18. The system of claim 14 wherein the current delivered through the reference electrodes is in the range of 1.0 mA to 10 mA.

19. The system of claim 14 wherein three reference electrodes are positioned at the distal end of the insufflation needle and are axially spaced apart from each other by about 2 to 6 mm.

* * * * *